US008609894B2

(12) United States Patent
Baumann et al.

(10) Patent No.: US 8,609,894 B2
(45) Date of Patent: Dec. 17, 2013

(54) PROCESS FOR PREPARING AMINOPOLYCARBOXYLATES

(75) Inventors: Robert Baumann, Mannheim (DE); Markus Christian Biel, Mannheim (DE); Axel Franzke, Mannheim (DE); Alfred Oftring, Bad Duerkheim (DE); Friedhelm Teich, Neckarhausen (DE); Paul Klingelhoefer, Mannheim (DE); Marie Katrin Schroeter, Dannstadt-Schauernheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/437,093

(22) Filed: Apr. 2, 2012

(65) Prior Publication Data

US 2012/0302783 A1 Nov. 29, 2012

Related U.S. Application Data

(60) Provisional application No. 61/488,829, filed on May 23, 2011.

(51) Int. Cl.
*C07C 51/21* (2006.01)

(52) U.S. Cl.
USPC ......................................................... 562/526

(58) Field of Classification Search
CPC ..................................................... C07C 227/02
See application file for complete search history.

(56) References Cited

U.S. PATENT DOCUMENTS

| 4,709,090 | A | 11/1987 | Nishibayashi et al. |
| 5,220,055 | A | 6/1993 | Urano et al. |
| 5,367,112 | A * | 11/1994 | Franczyk ..................... 562/526 |
| 5,916,840 | A | 6/1999 | Ebner et al. |
| 2003/0048413 | A1 | 3/2003 | Ross et al. |
| 2003/0097020 | A1 | 5/2003 | Franczyk, II et al. |
| 2005/0020850 | A1 | 1/2005 | Wessel et al. |
| 2011/0257431 | A1 | 10/2011 | Baumann et al. |

FOREIGN PATENT DOCUMENTS

| DE | 35 05 208 A1 | 3/1986 |
| EP | 0 201 957 A2 | 11/1986 |
| EP | 0 506 973 A1 | 10/1992 |
| JP | 11-158130 | 6/1999 |
| WO | 98/50150 | 11/1998 |
| WO | 00/66539 | 11/2000 |
| WO | 03/022140 A2 | 3/2003 |
| WO | 03/051513 A1 | 6/2003 |
| WO | 2011/113822 A1 | 9/2011 |
| WO | WO 2012/139842 A1 | 10/2012 |

OTHER PUBLICATIONS

White et al, Basic Energy Sciences Advisory Committee Subpanel Workshop Report, Opportunities for Catalysis in the 21st Century, 2002, pp. 1-47.*
International Search Report and Written Opinion issued Sep. 19, 2012 in Application No. PCT/EP2012/059126 (With English Translation of Category of Cited Documents).
U.S. Appl. No. 13/720,027, filed Dec. 19, 2012, Bou Chedid, et al.

* cited by examiner

*Primary Examiner* — Paul A Zucker
(74) *Attorney, Agent, or Firm* — Oblon, Spivak, McClelland, Maier & Neustadt, L.L.P.

(57) ABSTRACT

A process for preparing aminopolycarboxylates proceeding from the corresponding polyalkanolamines by oxidative dehydrogenation in the presence of a catalyst comprising 1 to 90% by weight of copper, based on the total weight of the catalyst, using a base, which comprises first performing a partial conversion of the polyalkanolamine to a reaction mixture comprising the aminopolycarboxylate at a temperature in the range from 140 to 180° C. until at least 10 to 90 mol% of the polyalkanolamine has been depleted, and then continuing the conversion at elevated temperature.

17 Claims, No Drawings

PROCESS FOR PREPARING AMINOPOLYCARBOXYLATES

This patent application claims the benefit of pending U.S. provisional patent application Ser. No. 61/488,829 filed 23 May 2011 incorporated in its entirety herein by reference.

Description

The invention relates to a process for preparing aminopolycarboxylates proceeding from the corresponding polyalkanolamines by catalytic oxidative dehydrogenation using a base.

The oxidative dehydrogenation of amino alcohols with alkali metal hydroxides is performed typically in an aqueous medium under pressure and at temperatures of 140 to 220° C. using copper-comprising catalysts. The catalysts consist, for example, of undoped or doped Raney copper (e.g. WO 00/066539). The dopants used are generally one or more metals, e.g. Pt, Fe, Cr, Mo, V, Bi, Sn, Sb, Pb, Ge or Ag.

In other cases, copper is applied directly or via anchor metals (e.g. Os, Ir, Rh, Pt or Pd) to alkali-stable supports (e.g. in WO 03/022140 or in WO 98/50150). Precipitated copper catalysts with further metal oxides have also been described (for example in WO 03/051513 (Cu, Fe) or in EP 0 506 973 (Cu, Zr, Ca)). There have also been isolated reports about conversion over noble metal systems (e.g. in EP 0 201 957).

A problem in the preparation especially of complex-forming aminopolycarboxylates such as methylglycinediacetic acid, glutamic acid diacetic acid, nitrilotriacetic acid, ethylenediaminetetraacetic acid and salts thereof from the corresponding polyalkanolamines is that a procedure corresponding to the prior art gives rise to by-products with lower efficacy. These include especially compounds which originate from C—N or C—C bond breaking. Using the example of the aminopolycarboxylate methylglycinediacetic acid trisodium salt (MGDA-Na$_3$), these are, for example, carboxymethylalanine disodium salt (C—N bond cleavage) and N-methyl-N-carboxymethylalanine (C—C bond cleavage).

It was therefore an object of the invention to provide a technically simple process for preparing aminopolycarboxylates proceeding from the corresponding polyalkanolamines by catalytic oxidative dehydrogenation, by which a product having a high purity directly and without complex further purification is obtained. This is equivalent to a high yield of at least 85 mol % of the desired aminopolycarboxylate or, in other words, the by-products should not make up more than 15% by weight in relation to the desired product.

The appropriate application may optionally be preceded by simple aftertreatment measures: in the case of a suspension method, the catalyst can be sedimented and/or filtered off. In addition, a desired water content can subsequently be established and/or bleaching can be performed, for example with hydrogen peroxide or UV light.

In addition to the salts (aminopolycarboxylates) themselves, the corresponding aminopolycarboxylic acids are also obtainable after acidification.

At the same time, the reaction conditions of the oxidative dehydrogenation should ensure a maximum period of recyclability of the catalyst used.

This object was achieved by a process for preparing aminopolycarboxylates proceeding from the corresponding polyalkanolamines by oxidative dehydrogenation in the presence of a catalyst comprising 1 to 90% by weight of copper, based on the total weight of the catalyst, using a base, which comprises first performing a partial conversion of the polyalkanolamine to a reaction mixture comprising the aminopolycarboxylate at a temperature in the range from 140 to 180° C. until at least 10 to 90 mol % of the polyalkanolamine has been depleted, and then continuing the conversion at elevated temperature.

The catalytic oxidative dehydrogenation of polyalkanolamines can be illustrated by the following reaction equation:

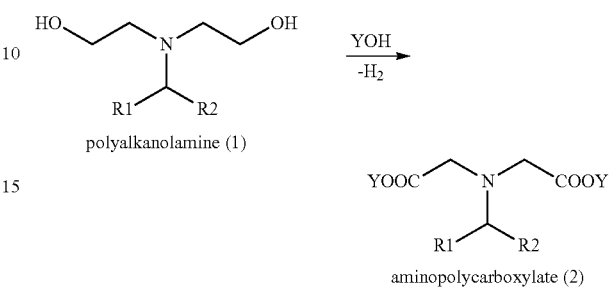

polyalkanolamine (1)

aminopolycarboxylate (2)

R1=H, —COOX where X=alkali metal, alkaline earth metal or hydrogen

R2=alkyl, alkenyl, alkynyl, aralkyl, hydroxyalkyl, hydroxyaralkyl, alkylene carboxyl, alkylene sulfonate or a bis(hydroxyethyl)aminoalkyklene radical Y=alkali metal or alkaline earth metal This reaction can be performed with Raney copper as a catalyst in good yields and good selectivity. However, it is not possible to conduct an economically viable process on the basis of this catalyst system since Raney copper is deactivated very rapidly at high temperatures and under basic conditions and can thus be recycled only to a very limited degree. For this reason, a suitable catalyst comprises not only copper but also further components in its active composition, which ensure a longer service life and higher stability, but can at the same time also reduce the selectivity of the dehydrogenation compared to Raney copper. For example, an execution in accordance with the prior art with a Cu/ZrO$_2$ catalyst affords a full conversion of the polyalkanolamine (1) ALDE-Na (R1=COONa, R2=CH$_3$) and thus exhibits a high catalytic activity in relation to the oxidative dehydrogenation, but leads only to an MGDA-Na$_3$ (methylglycinediacetic acid trisodium salt) yield of 72.5%. The main by-product at a yield of 25.6% is the carboxymethylalanine disodium salt originating from C—N bond cleavage, referred to hereinafter as CMA-Na$_2$. The formation of such degradation products in oxidative dehydrogenation is known from the literature.

In contrast, the inventors have found that the selectivity of the above dehydrogenation was enhanced significantly by selection of specific reaction conditions.

In relation to the reaction temperature, using the example of the polyalkanolamine (1) where R1=COONa and R2=CH$_3$ (referred to hereinafter as ALDE-Na$_3$), it has been found that, on performance of the reaction at a constant 170° C., less CMA-Na$_2$ is formed as a by-product (C—N bond breaking) than at a constant 190° C., but at the same time the reaction time needed for full conversion increases significantly. This is disadvantageous for economic reasons, since this method is associated with much lower space-time yields. However, it has been found that, surprisingly, CMA-Na$_2$ is formed predominantly from the polyalkanolamine used itself, and not from intermediates of the reaction. For this reason, to enhance the selectivity, it is sufficient to start the reaction at a lower temperature and, according to the desired selectivity, increase the reaction temperature directly or stepwise after conversion of the proportion of reactants needed for that purpose to intermediate or product, and thus to obtain reaction rate with virtually equal selectivity. In this way, the aminopolycarboxylate can be obtained in virtually the same selectivity but with much shorter reaction time compared to the reaction at constantly low temperature.

The catalytic oxidative dehydrogenation of the polyalkanolamine is thus performed in accordance with the invention in such a way that a partial conversion of the polyalkanolamine is first performed at a relatively low temperature in the range from 140 to 180° C. until at least 10 to 90 mol % of the polyalkanolamine has been depleted, and then the temperature is increased.

The temperature range within which the partial conversion is performed is preferably 150 to 175° C., especially 165 to 175° C.

Advantageously, the partial conversion is performed at a relatively low reaction temperature until the amount of the depleted polyalkanolamine is 30 to 90 mol %, preferably 50 to 80 mol %.

After the partial conversion, the temperature is preferably increased directly, i.e. in a single step, or stepwise, i.e. in several steps, to from 180 to 200° C., especially to from 185 to 195° C.

The catalytic oxidative dehydrogenation of the polyalkanolamine is preferably performed in the presence of water as a solvent.

It has been found that, in addition to the above-described influence of the temperature on the selectivity of the reaction, the concentration of water in the reaction mixture is also important.

The water used with preference as a solvent, with increasing concentration, surprisingly exerts not only a diluting effect which lowers the reaction rate, but also has an adverse effect on the selectivity of the reaction. Thus, it has been found that the CMA-Na$_2$ yield in the case of use of the ALDE-Na reactant in a solution comprising 58% by weight of water is already 12% with only 50% MGDA-Na$_3$ yield, whereas in a more concentrated method (37% by weight instead of 58% by weight of water in the reaction mixture) a similar CMA-Na$_2$ yield is attained at an MGDA-Na$_3$ yield of still 81%. Much lower water contents in the reaction mixture are more difficult to implement in practice since the catalyst can no longer be suspended in an optimal manner due to the viscosity of the reactants and products.

The process is therefore preferably performed in such a way that the concentration of the water in the reaction mixture is preferably 30 to 60% by weight, especially 40 to 55% by weight, based on the total weight of the reaction mixture.

It has additionally been found that, with rising catalyst concentration in the reaction mixture, not only the reaction rate of the oxidative dehydrogenation but surprisingly also the selectivity of the reaction increases, such that, for example, increasing the amount of catalyst from 3 g/mol of ALDE-Na (R1=COONa, R2=CH$_3$) to 40 g/mol of ALDE-Na causes the MGDA-Na$_3$ yield to rise from 72.5% to nearly 90% with equal conversion, compensated for by a fall in the yield of CMA-Na$_2$.

According to the invention, the process is thus preferably performed in such a way that the amount of catalyst used is such that it corresponds only to 0.40 g to 2.00 g of copper, preferably 1.00 g to 1.70 g of copper and more preferably 1.40 g to 1.60 g of copper per mole of hydroxyl group to be converted in the polyalkanolamine.

The ratio of the mass of MGDA-Na$_3$ to CMA-Na$_2$ in the reaction output of the oxidative dehydrogenation can be influenced significantly by the above conditions in favor of MGDA-Na$_3$ and therefore the product quality can be improved significantly.

Aminopolycarboxylates refer in the present context to aminocarboxylates having three or four deprotonated carboxylic acid groups. Aminopolycarboxylates having three deprotonated carboxylic acid groups are especially salts of methylglycinediacetic acid and of nitrilotriacetic acid; aminopolycarboxylates having four deprotonated carboxylic acid groups are especially salts of glutamic acid diacetic acid and ethylenediaminetetraacetic acid. On the basis of these structures, the aminopolycarboxylates can be used advantageously as complexing agents.

The polyalkanolamine is advantageously selected from the group of compounds with the general formula

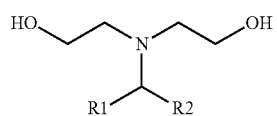

where R1=H or COOX where X=alkali metal, alkaline earth metal or hydrogen, and R2=an alkyl, alkenyl, alkynyl, aralkyl, hydroxyalkyl, hydroxyaralkyl, alkylene carboxyl, alkylene sulfonate or a bis(hydroxyethyl)aminoalkylene radical.

R2 is preferably a linear or branched alkyl radical which has 1 to 30 carbon atoms and may optionally also comprise rings, a linear or branched alkenyl radical which has 2 to 30 carbon atoms and may optionally also comprise rings, a linear or branched hydroxyalkyl radical having 1 to 30 carbon atoms, an alkylenecarboxylate radical having 2 to 30 carbon atoms, an alkylenesulfonate radical having 1 to 30 carbon atoms or a linear bis(hydroxyethyl)aminoalkylene radical having 1-10 carbon atoms.

Particular preference is given to compounds which derive from the amino acids alanine (R1=COOX; R2=CH$_3$), glutamic acid (R1=COOX; R2=CH$_2$—CH$_2$—COOX) and serine (R1=COOX; R2=CH$_2$—OH), or from ethylenediamine (R1=H; R2=CH$_2$—N(CH$_2$—CH$_2$—OH)$_2$) or triethanolamine (R1=H, R2=CH$_2$—OH).

If the polyalkanolamine is a chiral compound with at least one asymmetric carbon atom, it can be used in enantiomerically pure, scalemic or else racemic form.

The base used is preferably an alkali metal or alkaline earth metal hydroxide, especially sodium hydroxide or potassium hydroxide. It is advantageously used as an aqueous solution, preferably as a 50% by weight aqueous solution.

The reaction pressure is advantageously adjusted such that the hydrogen formed is removed continuously. Preference is given to a pressure of standard pressure to 100 bar absolute, more preferably of 5-50 bar absolute and most preferably of 8-20 bar absolute.

The process is preferably performed in batchwise mode.

A process in which the polyalkanolamine is prepared by alkoxylation of the parent amine or of the parent amino acid and is dehydrogenated directly is particularly preferred. Direct dehydrogenation means that no apparatus removal, based on different boiling points, of substances with boiling points greater than 200° C. (at standard pressure) is effected between the alkoxylation and the oxidative dehydrogenation. This is simpler in apparatus terms and thus dispenses with one operation with comparably good end product quality.

It is possible with preference to proceed here by the process described in the European patent application numbered EP 11 162 091.0, which proceeds from an amino acid which is reacted in a first process step with ethylene oxide to give an intermediate mixture comprising the corresponding dialkanolamine, and then the intermediate mixture is converted catalytically in a second process step using a base to the corresponding aminopolycarboxylate, the amino acid before the reaction with ethylene oxide in the first process step being supplied to a partial neutralization with 0.70 to 0.99 equivalent of base per acid group, or an amino acid already partly neutralized with 0.70 to 0.99 equivalent of base per acid group being used in the first process step.

The catalyst comprising 1 to 90% by weight of copper, based on the total weight thereof, can be used, for example, in the form of powder or shaped bodies (e.g. extrudates, tablets, etc.), as an unsupported catalyst or as a supported catalyst.

The end product of the process is used, optionally after the simple aftertreatment measures described at the outset, for example as an additive for industrial cleaning formulations for hard surfaces of metal, plastic, coating material or glass, in alkaline cleaning formulations for the drinks and foods industry, especially for bottle cleaning in the drinks industry and for apparatus cleaning in dairies, in breweries, in the preserves industry, in the bakery industry, in the sugar industry, in the fat-processing industry and in the meat-processing industry, in dishware cleaning formulations, especially in phosphate-free compositions for machine dishwashing in machine dishwashers in the household or in commercial premises, for example large kitchens or restaurants, in bleaching baths in the paper industry, in photographic bleaching and bleach fixing baths, in pretreatment and bleaching in the textile industry, in electrolytic baths for masking of contaminating heavy metal cations, and also in the field of plant foods for remedying heavy metal deficits as copper, iron, manganese and/or zinc complexes. In principle, use is advantageous wherever precipitations of calcium, magnesium or heavy metal salts disrupt industrial processes and should therefore be prevented (prevention of deposits and encrustations in tanks, pipelines, spray nozzles or generally on smooth surfaces). The aminopolycarboxylates can also be used for stabilization of phosphates in alkaline degreasing baths and for prevention of the precipitation of lime soaps, in order thus to prevent the tarnishing of non-iron surfaces and to prolong the service life of alkaline cleaning baths. In addition, they find use in pulverulent or liquid detergent formulations for textile washing as builders and preservatives. In soaps, they prevent metal-catalyzed oxidative decompositions, and also in pharmaceuticals, cosmetics and foods.

The present invention is illustrated in detail hereinafter by nonlimiting examples:

Preparation of the Aqueous Polyalkanolamine Starting Solution 4.365 kg (49.00 mol) of alanine were suspended in 2.623 kg of water, and 3.897 kg (49.00 mol) of 50.3% by weight sodium hydroxide solution were added. The resulting mixture was introduced into a 20 l autoclave (2.4610 material) and, after appropriate inertization, nitrogen was injected to 20 bar. Subsequently, 4.749 kg (107.8 mol) of ethylene oxide were metered in at 40-45° C. within 12.5 h and the mixture was stirred at this temperature for a further 3 h. After the removal of the unconverted residues of ethylene oxide, the autoclave was emptied. In this way, 15.634 kg of aqueous reaction output were obtained as a clear colorless viscous solution.

COMPARATIVE EXAMPLE 1

Oxidative Dehydrogenation with $Cu/ZrO_2$ as a Catalyst 314 g (0.99 mol based on alanine) of the above aqueous polyalkanolamine starting solution were initially charged with 197.9 g (2.39 mol) of 50% by weight sodium hydroxide solution, 32 g of water and 3 g of $Cu/ZrO_2$ (reworking of patent DE 3505208) in a 1.7 l autoclave (2.4610 material). The reactor was closed, nitrogen was injected to 5 bar and then the reactor was heated to 190° C. within 2.25 h. This temperature was maintained for 72 h. The stirrer speed was 500 rpm over the entire experimental duration. The hydrogen formed was removed continuously via a 10 bar pressure relief valve. After the end of the experiment, the reactor was purged with nitrogen at room temperature, the reaction output was diluted with 411 g of water and then the reactor was emptied. The product was obtained as a clear colorless viscous solution. By means of HPLC, a yield (=selectivity*conversion) of methylglycine-N,N-diacetic acid trisodium salt (MGDA-$Na_3$) of 72.5% of theory based on alanine used was determined. The yield of carboxymethylalanine disodium salt (CMA-$Na_2$) was 25.6% of theory based on alanine used.

The ratio of the mass of MGDA-$Na_3$ obtained to the mass of CMA-$Na_2$ obtained is thus 1:0.25.

COMPARATIVE EXAMPLE 2

Oxidative Dehydrogenation with $Cu/ZrO_2$ as a Catalyst 316 g (0.99 mol based on alanine) of the above aqueous polyalkanolamine starting solution were initially charged with 181.6 g (2.27 mol) of 50% by weight sodium hydroxide solution, 32 g of water and 30 g of $Cu/ZrO_2$ (reworking of patent DE 3505208) in a 1.7 l autoclave (2.4610 material). The reactor was closed, nitrogen was injected to 5 bar and then the reactor was heated to 190° C. within 2.25 h. This temperature was maintained for 16 h. The stirrer speed was 500 rpm over the entire experimental duration. The hydrogen formed was removed continuously via a 10 bar pressure relief valve. After the end of the experiment, the reactor was purged with nitrogen at room temperature, the reaction output was diluted with 407 g of water and then the reactor was emptied. The product was obtained as a clear colorless viscous solution. By means of HPLC, a yield (=selectivity*conversion) of methylglycine-N,N-diacetic acid trisodium salt (MGDA-$Na_3$) of 85.8% of theory based on alanine used was determined. The yield of carboxymethylalanine disodium salt (CMA-$Na_2$) was 8.6% of theory based on alanine used.

The ratio of the mass of MGDA-$Na_3$ obtained to the mass of CMA-$Na_2$ obtained is thus 1:0.07.

The space-time yield was 7.42 g/l*h.

COMPARATIVE EXAMPLE 3

Oxidative Dehydrogenation with $Cu/ZrO_2$ as a Catalyst 316 g (0.99 mol based on alanine) of the above aqueous polyalkanolamine starting solution were initially charged with 181.9 g (2.28 mol) of 50% by weight sodium hydroxide solution, 32 g of water and 30 g of $Cu/ZrO_2$ (reworking of patent DE 3505208) in a 1.7 l autoclave (2.4610 material). The reactor was closed, nitrogen was injected to 5 bar and then the reactor was heated to 180° C. within 2.25 h. This temperature was maintained for 24 h. The stirrer speed was 500 rpm over the entire experimental duration. The hydrogen formed was removed continuously via a 10 bar pressure relief valve. After the end of the experiment, the reactor was purged with nitrogen at room temperature, the reaction output was diluted with 400 g of water and then the reactor was emptied. The product was obtained as a clear colorless viscous solution. By means of HPLC, a yield (=selectivity*conversion) of methylglycine-N,N-diacetic acid trisodium salt (MGDA-$Na_3$) of 88.1% of theory based on alanine used was determined. The yield of carboxymethylalanine disodium salt (CMA-$Na_2$) was 6.8% of theory based on alanine used.

The ratio of the mass of MGDA-$Na_3$ obtained to the mass of CMA-$Na_2$ obtained is thus 1:0.05.

The space-time yield was 5.30 g/l*h.

COMPARATIVE EXAMPLE 4

Oxidative Dehydrogenation with Cu/$ZrO_2$ as a Catalyst 316 g (0.99 mol based on alanine) of the above aqueous polyalkanolamine starting solution were initially charged with 181.1 g (2.26 mol) of 50% by weight sodium hydroxide solution, 32 g of water and 30 g of Cu/$ZrO_2$ (reworking of patent DE 3505208) in a 1.7 l autoclave (2.4610 material). The reactor was closed, nitrogen was injected to 5 bar and then the reactor was heated to 170° C. within 2.25 h. This temperature was maintained for 60 h. The stirrer speed was 500 rpm over the entire experimental duration. The hydrogen formed was removed continuously via a 10 bar pressure relief valve. After the end of the experiment, the reactor was purged with nitrogen at room temperature, the reaction output was diluted with 444 g of water and then the reactor was emptied. The product was obtained as a clear colorless viscous solution. By means of HPLC, a yield (=selectivity*conversion) of methylglycine-N,N-diacetic acid trisodium salt (MGDA-$Na_3$) of 89.6% of theory based on alanine used was determined. The yield of carboxymethylalanine disodium salt (CMA-$Na_2$) was 4.3% of theory based on alanine used.

The ratio of the mass of MGDA-$Na_3$ obtained to the mass of CMA-$Na_2$ obtained is thus 1:0.03.

The space-time yield was 2.27 g/l*h.

Comparative examples 2 to 4 show that performance of the oxidative dehydrogenation at lower reaction temperatures results in an increase in the selectivity for MGDA-$Na_3$. At the same time, however, this is associated with much longer reaction times and hence lower space-time yields.

EXAMPLE 1 (INVENTIVE)

Oxidative Dehydrogenation with Cu/$ZrO_2$ as a Catalyst 316 g (0.99 mol based on alanine) of the above aqueous polyalkanolamine starting solution were initially charged with 182.3 g (2.28 mol) of 50% by weight sodium hydroxide solution, 32 g of water and 30 g of Cu/$ZrO_2$ (reworking of patent DE 3505208) in a 1.7 l autoclave (2.4610 material). The reactor was closed, nitrogen was injected to 5 bar and then the reactor was heated to 170° C. within 2.25 h. This temperature was maintained for 12 h, after which 90 mol % of the polyalkanolamine had been depleted. Thereafter, the mixture was heated to 180° C. within 30 minutes and this temperature was subsequently maintained for 4 h. Thereafter, the mixture was heated to 190° C. within 30 minutes and this temperature was subsequently maintained for 3 h. The stirrer speed was 500 rpm over the entire experimental duration. The hydrogen formed was removed continuously via a 10 bar pressure relief valve. After the end of the experiment, the reactor was purged with nitrogen at room temperature, the reaction output was diluted with 419 g of water and then the reactor was emptied. The product was obtained as a clear colorless viscous solution. By means of HPLC, a yield (=selectivity*conversion) of methylglycine-N,N-diacetic acid trisodium salt (MGDA-$Na_3$) of 89.4% of theory based on alanine used was determined. The yield of carboxymethylalanine disodium salt (CMA-$Na_2$) was 5.0% of theory based on alanine used.

The ratio of the mass of MGDA-$Na_3$ obtained to the mass of CMA-$Na_2$ obtained is thus 1:0.04.

The space-time yield was 6.34 g/l*h.

EXAMPLE 2 (INVENTIVE)

Oxidative Dehydrogenation with Cu/$ZrO_2$ as a Catalyst 316 g (0.99 mol based on alanine) of the above aqueous polyalkanolamine starting solution were initially charged with 182.0 g (2.28 mol) of 50% by weight sodium hydroxide solution, 32 g of water and 30 g of Cu/$ZrO_2$ (reworking of patent DE 3505208) in a 1.7 l autoclave (2.4610 material). The reactor was closed, nitrogen was injected to 5 bar and then the reactor was heated to 170° C. within 2.25 h. This temperature was maintained for 6 h, after which 70 mol % of the polyalkanolamine had been depleted. Thereafter, the mixture was heated to 180° C. within 30 minutes and this temperature was subsequently maintained for 4 h. Thereafter, the mixture was heated to 190° C. within 30 minutes and this temperature was subsequently maintained for 3 h. The stirrer speed was 500 rpm over the entire experimental duration. The hydrogen formed was removed continuously via a 10 bar pressure relief valve. After the end of the experiment, the reactor was purged with nitrogen at room temperature, the reaction output was diluted with 394 g of water and then the reactor was emptied. The product was obtained as a clear colorless viscous solution. By means of HPLC, a yield (=selectivity*conversion) of methylglycine-N,N-diacetic acid trisodium salt (MGDA-$Na_3$) of 90.0% of theory based on alanine used was determined. The yield of carboxymethylalanine disodium salt (CMA-$Na_2$) was 5.2% of theory based on alanine used.

The ratio of the mass of MGDA-$Na_3$ obtained to the mass of CMA-$Na_2$ obtained is thus 1:0.04.

The space-time yield was 8.75 g/l*h.

EXAMPLE 3 (INVENTIVE)

Oxidative Dehydrogenation with Cu/$ZrO_2$ as a Catalyst 316 g (0.99 mol based on alanine) of the above aqueous polyalkanolamine starting solution were initially charged with 182.0 g (2.28 mol) of 50% by weight sodium hydroxide solution, 32 g of water and 30 g of Cu/$ZrO_2$ (reworking of patent DE 3505208) in a 1.7 l autoclave (2.4610 material). The reactor was closed, nitrogen was injected to 5 bar and then the reactor was heated to 170° C. within 2.25 h. This temperature was maintained for 6 h, after which 70 mol % of the polyalkanolamine had been depleted. Thereafter, the mixture was heated to 180° C. within 30 minutes and this temperature was subsequently maintained for 2 h. Thereafter, the mixture was heated to 190° C. within 30 minutes and this temperature was subsequently maintained for 3 h. The stirrer speed was 500 rpm over the entire experimental duration. The hydrogen formed was removed continuously via a 10 bar pressure relief valve. After the end of the experiment, the reactor was purged with nitrogen at room temperature, the reaction output was diluted with 423 g of water and then the reactor was emptied. The product was obtained as a clear colorless viscous solution. By means of HPLC, a yield (=selectivity*conversion) of methylglycine-N,N-diacetic acid trisodium salt (MGDA-Na$_3$) of 88.8% of theory based on alanine used was determined. The yield of carboxymethylalanine disodium salt (CMA-Na$_2$) was 5.6% of theory based on alanine used.

The ratio of the mass of MGDA-Na$_3$ obtained to the mass of CMA-Na$_2$ obtained is thus 1:0.04.

The space-time yield was 9.84 g/l*h.

Examples 1-3 show that an inventive procedure leads to the same yields of product of value within shorter reaction times than a constant procedure at low temperature and with a correspondingly longer reaction time.

COMPARATIVE EXAMPLE 5

Oxidative Dehydrogenation with Cu/ZrO$_2$ as a Catalyst 316 g (0.99 mol based on alanine) of the above aqueous polyalkanolamine starting solution were initially charged with 182.4 g (2.28 mol) of 50% by weight sodium hydroxide solution, 182 g of water and 10 g of Cu/ZrO$_2$ (reworking of patent DE 3505208) in a 1.7 l autoclave (2.4610 material). The reactor was closed, nitrogen was injected to 5 bar and then the reactor was heated to 190° C. within 2.25 h. This temperature was maintained for 16 h. The stirrer speed was 500 rpm over the entire experimental duration. The hydrogen formed was removed continuously via a 10 bar pressure relief valve. After the end of the experiment, the reactor was purged with nitrogen at room temperature, the reaction output was diluted with 256 g of water and then the reactor was emptied. The product was obtained as a clear colorless viscous solution. By means of HPLC, a yield (=selectivity*conversion) of methylglycine-N,N-diacetic acid trisodium salt (MGDA-Na$_3$) of 49.4% of theory based on alanine used was determined. The yield of carboxymethylalanine disodium salt (CMA-Na$_2$) was 12.9% of theory based on alanine used.

The ratio of the mass of MGDA-Na$_3$ obtained to the mass of CMA-Na$_2$ obtained is thus 1:0.18.

COMPARATIVE EXAMPLE 6

Oxidative Dehydrogenation with Cu/ZrO$_2$ as a Catalyst 316 g (0.99 mol based on alanine) of the above aqueous polyalkanolamine starting solution were initially charged with 181.9 g (2.28 mol) of 50% by weight sodium hydroxide solution, 32 g of water and 10 g of Cu/ZrO$_2$ (reworking of patent DE 3505208) in a 1.7 l autoclave (2.4610 material). The reactor was closed, nitrogen was injected to 5 bar and then the reactor was heated to 190° C. within 2.25 h. This temperature was maintained for 16 h. The stirrer speed was 500 rpm over the entire experimental duration. The hydrogen formed was removed continuously via a 10 bar pressure relief valve. After the end of the experiment, the reactor was purged with nitrogen at room temperature, the reaction output was diluted with 425 g of water and then the reactor was emptied. The product was obtained as a clear colorless viscous solution. By means of HPLC, a yield (=selectivity*conversion) of methylglycine-N,N-diacetic acid trisodium salt (MGDA-Na$_3$) of 76.2% of theory based on alanine used was determined. The yield of carboxymethylalanine disodium salt (CMA-Na$_2$) was 16.0% of theory based on alanine used.

The ratio of the mass of MGDA-Na$_3$ obtained to the mass of CMA-Na$_2$ obtained is thus 1:0.15.

COMPARATIVE EXAMPLE 7

Oxidative Dehydrogenation with Cu/ZrO$_2$ as a Catalyst 253 g (0.98 mol based on alanine) of the above aqueous polyalkanolamine starting solution concentrated by distillation were initially charged with 182.3 g (2.28 mol) of 50% by weight sodium hydroxide solution, 37 g of water and 10 g of Cu/ZrO$_2$ (reworking of patent DE 3505208) in a 1.7 l autoclave (2.4610 material). The reactor was closed, nitrogen was injected to 5 bar and then the reactor was heated to 190° C. within 2.25 h. This temperature was maintained for 16 h. The stirrer speed was 500 rpm over the entire experimental duration. The hydrogen formed was removed continuously via a 10 bar pressure relief valve. After the end of the experiment, the reactor was purged with nitrogen at room temperature, the reaction output was diluted with 431 g of water and then the reactor was emptied. The product was obtained as a clear colorless viscous solution. By means of HPLC, a yield (=selectivity*conversion) of methylglycine-N,N-diacetic acid trisodium salt (MGDA-Na$_3$) of 81.8% of theory based on alanine used was determined. The yield of carboxymethylalanine disodium salt (CMA-Na$_2$) was 13.9% of theory based on alanine used.

The ratio of the mass of MGDA-Na$_3$ obtained to the mass of CMA-Na$_2$ obtained is thus 1:0.12.

COMPARATIVE EXAMPLE 8

Oxidative Dehydrogenation with Cu/ZrO$_2$ as a Catalyst 274 g (0.98 mol based on alanine) of the above aqueous polyalkanolamine starting solution concentrated by distillation were initially charged with 182.6 g (2.28 mol) of 50% by weight sodium hydroxide solution and 10 g of Cu/ZrO$_2$ (reworking of patent DE 3505208) in a 1.7 l autoclave (2.4610 material). The reactor was closed, nitrogen was injected to 5 bar and then the reactor was heated to 190° C. within 2.25 h. This temperature was maintained for 16 h. The stirrer speed was 500 rpm over the entire experimental duration. The hydrogen formed was removed continuously via a 10 bar pressure relief valve. After the end of the experiment, the reactor was purged with nitrogen at room temperature, the reaction output was diluted with 471 g of water and then the reactor was emptied. The product was obtained as a clear colorless viscous solution. By means of HPLC, a yield (=selectivity*conversion) of methylglycine-N,N-diacetic acid trisodium salt (MGDA-Na$_3$) of 70.4% of theory based on alanine used was determined. The yield of carboxymethylalanine disodium salt (CMA-Na$_2$) was 7.8% of theory based on alanine used.

The ratio of the mass of MGDA-Na$_3$ obtained to the mass of CMA-Na$_2$ obtained is thus 1:0.08.

Comparative examples 5 to 8 show that the water content in the reaction mixture is important for the selectivity of the oxidative dehydrogenation, but sufficient selectivity cannot be achieved via the adjustment of the water content alone.

COMPARATIVE EXAMPLE 9

Oxidative Dehydrogenation with Cu/ZrO$_2$ as a Catalyst 316 g (0.99 mol based on alanine) of the above aqueous polyalkanolamine starting solution were initially charged with 181.7 g (2.27 mol) of 50% by weight sodium hydroxide solution, 32 g of water and 10 g of Cu/ZrO₂ (reworking of patent DE 3505208) in a 1.7 l autoclave (2.4610 material). The reactor was closed, nitrogen was injected to 5 bar and then the reactor was heated to 190° C. within 2.25 h. This temperature was maintained for 16 h. The stirrer speed was 500 rpm over the entire experimental duration. The hydrogen formed was removed continuously via a 10 bar pressure relief valve. After the end of the experiment, the reactor was purged with nitrogen at room temperature, the reaction output was diluted with 404 g of water and then the reactor was emptied. The product was obtained as a clear colorless viscous solution. By means of HPLC, a yield (=selectivity*conversion) of methylglycine-N,N-diacetic acid trisodium salt (MGDA-Na₃) of 77.2% of theory based on alanine used was determined. The yield of carboxymethylalanine disodium salt (CMA-Na₂) was 18.2% of theory based on alanine used.

The ratio of the mass of MGDA-Na₃ obtained to the mass of CMA-Na₂ obtained is thus 1:0.17.

COMPARATIVE EXAMPLE 10

Oxidative Dehydrogenation with Cu/ZrO₂ as a Catalyst 316 g (0.99 mol based on alanine) of the above aqueous polyalkanolamine starting solution were initially charged with 182.1 g (2.28 mol) of 50% by weight sodium hydroxide solution, 32 g of water and 20 g of Cu/ZrO₂ (reworking of patent DE 3505208) in a 1.7 l autoclave (2.4610 material). The reactor was closed, nitrogen was injected to 5 bar and then the reactor was heated to 190° C. within 2.25 h. This temperature was maintained for 16 h. The stirrer speed was 500 rpm over the entire experimental duration. The hydrogen formed was removed continuously via a 10 bar pressure relief valve. After the end of the experiment, the reactor was purged with nitrogen at room temperature, the reaction output was diluted with 411 g of water and then the reactor was emptied. The product was obtained as a clear colorless viscous solution. By means of HPLC, a yield (=selectivity*conversion) of methylglycine-N,N-diacetic acid trisodium salt (MGDA-Na₃) of 77.8% of theory based on alanine used was determined. The yield of carboxymethylalanine disodium salt (CMA-Na₂) was 11.3% of theory based on alanine used.

The ratio of the mass of MGDA-Na₃ obtained to the mass of CMA-Na₂ obtained is thus 1:0.10.

COMPARATIVE EXAMPLE 11

Oxidative Dehydrogenation with Cu/ZrO₂ as a Catalyst 316 g (0.99 mol based on alanine) of the above aqueous polyalkanolamine starting solution were initially charged with 181.6 g (2.27 mol) of 50% by weight sodium hydroxide solution, 32 g of water and 30 g of Cu/ZrO₂ (reworking of patent DE 3505208) in a 1.7 l autoclave (2.4610 material). The reactor was closed, nitrogen was injected to 5 bar and then the reactor was heated to 190° C. within 2.25 h. This temperature was maintained for 16 h. The stirrer speed was 500 rpm over the entire experimental duration. The hydrogen formed was removed continuously via a 10 bar pressure relief valve. After the end of the experiment, the reactor was purged with nitrogen at room temperature, the reaction output was diluted with 407 g of water and then the reactor was emptied. The product was obtained as a clear colorless viscous solution. By means of HPLC, a yield of methylglycine-N,N-diacetic acid trisodium salt (MGDA-Na₃) of 85.8% of theory based on alanine used was determined. The yield of carboxymethylalanine disodium salt (CMA-Na₂) was 8.6% of theory based on alanine used.

The ratio of the mass of MGDA-Na₃ obtained to the mass of CMA-Na₂ obtained is thus 1:0.07.

COMPARATIVE EXAMPLE 12

Oxidative Dehydrogenation with Cu/ZrO₂ as a Catalyst 316 g (0.99 mol based on alanine) of the above aqueous polyalkanolamine starting solution were initially charged with 181.8 g (2.27 mol) of 50% by weight sodium hydroxide solution, 32 g of water and 40 g of Cu/ZrO₂ (reworking of patent DE 3505208) in a 1.7 l autoclave (2.4610 material). The reactor was closed, nitrogen was injected to 5 bar and then the reactor was heated to 190° C. within 2.25 h. This temperature was maintained for 16 h. The stirrer speed was 500 rpm over the entire experimental duration. The hydrogen formed was removed continuously via a 10 bar pressure relief valve. After the end of the experiment, the reactor was purged with nitrogen at room temperature, the reaction output was diluted with 400 g of water and then the reactor was emptied. The product was obtained as a clear colorless viscous solution. By means of HPLC, a yield (=selectivity*conversion) of methylglycine-N,N-diacetic acid trisodium salt (MGDA-Na₃) of 89.5% of theory based on alanine used was determined. The yield of carboxymethylalanine disodium salt (CMA-Na₂) was 7.5% of theory based on alanine used.

The ratio of the mass of MGDA-Na₃ obtained to the mass of CMA-Na₂ obtained is thus 1:0.06.

Comparative examples 9 to 12 show that rising amounts of catalyst used increase not only the rate but also the selectivity of the oxidative dehydrogenation. However, sufficient selectivity cannot be achieved via the adjustment of the amount of catalyst alone.

The invention claimed is:

1. A process for preparing aminopolycarboxylates proceeding from the corresponding polyalkanolamines by oxidative dehydrogenation in the presence of a catalyst comprising 1 to 90% by weight of copper, based on the total weight of the catalyst, using a base, which comprises first performing a partial conversion of the polyalkanolamine to a reaction mixture comprising the aminopolycarboxylate at a temperature in the range from 140 to 180° C. until at least 10 to 90 mol% of the polyalkanolamine has been depleted, and then continuing the conversion at elevated temperature, wherein the catalyst comprises Cu/ZrO₂.

2. The process according to claim 1, wherein the alkanolamine is selected from the group of the polyalkanolamines of the formula:

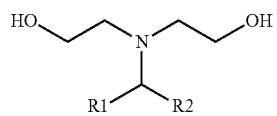

where R1=H or COOX where X=alkali metal, alkaline earth metal or hydrogen, and R2=an alkyl, alkenyl, alkynyl, aralkyl, hydroxyalkyl, hydroxyaralkyl, alkylene carboxyl, alkylene sulfonate or a bis- (hydroxyethyl) aminoalkylene radical.

3. The process according to claim 2, wherein R1=H and R2=—CH$_2$OH, or R1=COOX and R2=CH$_3$, or R1=COOX and R2=CH$_2$—CH$_2$—COOX, or R1=H and R2=CH$_2$—N(C$_2$H$_4$OH)$_2$.

4. The process according to claim 1, wherein the temperature range within which the partial conversion is performed is 150 to 175° C.

5. The process according to claim 1, wherein the amount of the depleted polyalkanolamine before the increase in the reaction temperature is 30 to 90 mol%.

6. The process according to claim 1, wherein the temperature is increased after the partial conversion directly or stepwise to from 180 to 200° C.

7. The process according to claim 1, wherein the catalytic oxidative dehydrogenation is performed in the presence of water as a solvent.

8. The process according to claim 7, wherein the concentration of the water in the reaction mixture is 30 to 80% by weight.

9. The process according to claim 1, wherein the amount of catalyst used is such that it corresponds to 0.40 g to 2.00 g of copper, per mole of hydroxyl group to be converted in the polyalkanolamine.

10. The process according to claim 1, wherein the polyalkanolamine used is an intermediate mixture comprising a dialkanolamine which is obtained by ethoxylating an amino acid, the amino acid before the reaction with ethylene oxide being supplied to a partial neutralization with 0.70 to 0.99 equivalent of base per acid group, or an amino acid already partly neutralized with 0.70 to 0.99 equivalent of base per acid group is supplied to the reaction with ethylene oxide.

11. The process according to claim 4, wherein the temperature range within which the partial conversion is performed is 165 to 175° C.

12. The process according to claim 5, wherein the amount of the depleted polyalkanolamine before the increase in the reaction temperature is 50 to 80 mol%.

13. The process according to claim 6, wherein the temperature is increased after the partial conversion directly or stepwise to from 185 to 195° C.

14. The process according to claim 8, wherein the concentration of the water in the reaction mixture is 35 to 60% by weight.

15. The process according to claim 9, wherein the amount of catalyst used is such that it corresponds to 1.00 g to 1.70 g of copper per mole of hydroxyl group to be converted in the polyalkanolamine.

16. The process according to claim 14, wherein the concentration of the water in the reaction mixture is 40 to 55% by weight.

17. The process according to claim 15, wherein the amount of catalyst used is such that it corresponds to 1.40 g to 1.60 g of copper, per mole of hydroxyl group to be converted in the polyalkanolamine.

* * * * *